(12) United States Patent
Rietzel

(10) Patent No.: US 7,560,698 B2
(45) Date of Patent: Jul. 14, 2009

(54) MEDICAL IMAGING UNIT

(75) Inventor: Eike Rietzel, Darmstadt (DE)

(73) Assignee: Siemens Aktiengesellschaft, Munich (DE)

(*) Notice: Subject to any disclaimer, the term of this patent is extended or adjusted under 35 U.S.C. 154(b) by 33 days.

(21) Appl. No.: 11/897,559

(22) Filed: Aug. 31, 2007

(65) Prior Publication Data
US 2008/0061241 A1 Mar. 13, 2008

(30) Foreign Application Priority Data
Sep. 11, 2006 (DE) .................. 10 2006 042 572

(51) Int. Cl.
*G01T 1/164* (2006.01)
(52) U.S. Cl. .................. 250/363.03
(58) Field of Classification Search . 250/363.01–363.1; 378/98.8, 58, 59, 167, 15; 600/407, 428, 600/425
See application file for complete search history.

(56) References Cited

U.S. PATENT DOCUMENTS

| | | | |
|---|---|---|---|
| 5,338,936 A | 8/1994 | Gullberg et al. | |
| 5,420,427 A * | 5/1995 | Morgan et al. | 250/360.1 |
| 6,303,935 B1 * | 10/2001 | Engdahl et al. | 250/363.03 |
| 6,373,060 B1 * | 4/2002 | Yamakawa et al. | 250/363.08 |
| 6,661,866 B1 | 12/2003 | Limkeman et al. | |
| 7,292,673 B2 | 11/2007 | Kröner et al. | |
| 2003/0014132 A1 | 1/2003 | Ohba et al. | |
| 2003/0128801 A1 | 7/2003 | Eisenberg et al. | |
| 2004/0022350 A1 * | 2/2004 | Gregerson et al. | 378/15 |
| 2004/0097800 A1 | 5/2004 | Crosetto | |
| 2004/0113099 A1 * | 6/2004 | Eickhoff et al. | 250/492.3 |
| 2004/0195512 A1 | 10/2004 | Crosetto | |
| 2004/0210126 A1 * | 10/2004 | Hajaj et al. | 600/407 |
| 2005/0082487 A1 | 4/2005 | Amano | |
| 2007/0025522 A1 * | 2/2007 | Fenster et al. | 378/167 |
| 2007/0055145 A1 * | 3/2007 | Zelnik et al. | 600/428 |
| 2007/0100225 A1 | 5/2007 | Maschke | |

FOREIGN PATENT DOCUMENTS

| | | |
|---|---|---|
| DE | 44 06 996 A1 | 9/1994 |
| DE | 103 39 493 A1 | 3/2004 |
| DE | 10 2004 049 915 A1 | 5/2006 |
| DE | 10 2005 048 853 S1 | 4/2007 |

OTHER PUBLICATIONS

European Patent Office Action and Search Report dated Jan. 21, 2008 for EP 07 11 2161 and English translation.

* cited by examiner

*Primary Examiner*—David P Porta
*Assistant Examiner*—Kiho Kim
(74) *Attorney, Agent, or Firm*—Brinks, Hofer, Gilson & Lione

(57) ABSTRACT

A medical imaging unit is provided. The medical imaging unit include a tomography device for 3D imaging and a PET system for positron emission tomography. The PET system includes a detector ring that has an angular region that is without detector elements.

17 Claims, 1 Drawing Sheet

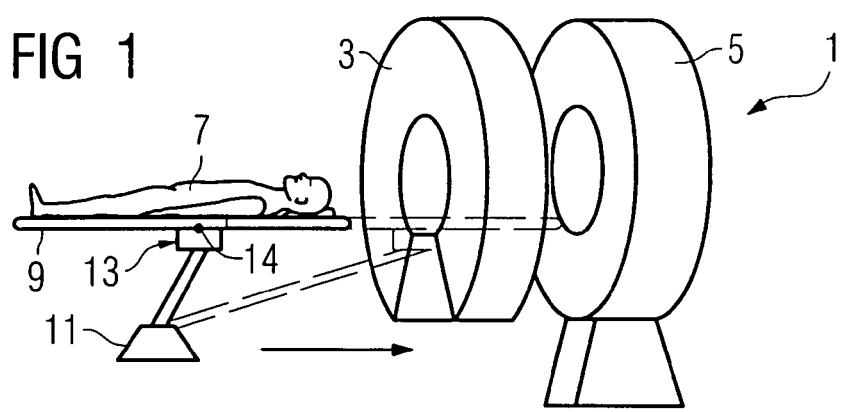
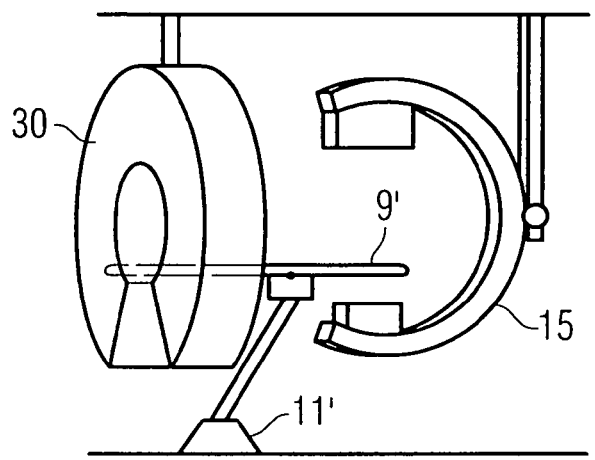
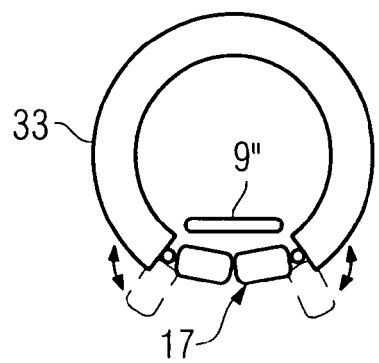
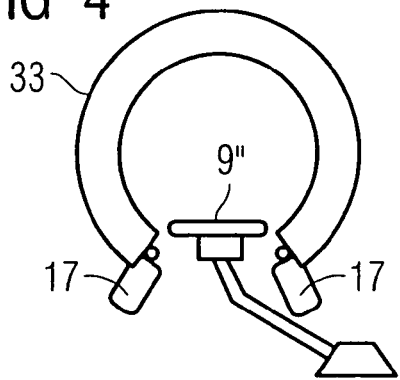
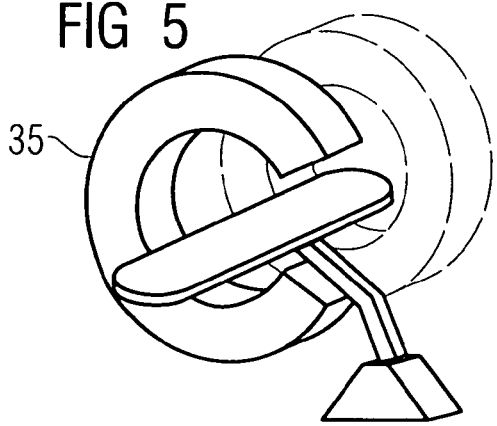

MEDICAL IMAGING UNIT

The present patent document claims the benefit of the filing date of DE 10 2006 042 572.3, filed Sep. 11, 2006.

BACKGROUND

The present embodiments relate to a medical imaging unit having a tomography device for 3D imaging and having a PET system for positron emission tomography.

DE 103 39 493 discloses a PET-CT scanner. US 2003/0014132 discloses a PET unit.

During positron emission tomography (PET), a patient is injected with a tracer, such as $^{18}$F-FDG (fluorodeoxyglucose), by mixing a radionuclide that has a comparatively short half-life with a carrier substance. The tracer accumulates in certain organs and cellular tissues and decomposes, emitting positrons. The enrichment may occur in active cancer cells.

After a relatively short distance, typically 1 mm, a positron liberated (emitted) in the process of radioactive decomposition interacts with an electron, whereupon both particles are destroyed and two gamma quanta, with an energy of 511 keV each, are emitted in diametrically opposite directions. These annihilation quanta may be proven to exist with spatial and chronological resolution in a detector ring, surrounding the object of the examination, such as the patient. The ring includes one or more gamma detectors located adjacent one another that may be read out individually. By means of coincidence collimation in an electronic evaluation unit behind the detectors, the site of the electron-positron annihilation, on which the counter events are each based, may be ascertained along the imaginary line between the signal-emitting detector elements, known as the line of response. The emission of the gamma radiation takes place isotropically. All the directions of emission of gamma radiation, statistically, are equally probable. From a statistically significant large number of counter events, the spatial frequency distribution of the radioactive decomposition processes and the distribution of the tracer in the body may be derived. From this kind of 3D volumetric data set, arbitrary two-dimensional PET slice images may be generated.

PET is a functional imaging process that may reproduce and display biochemical and physiological processes in the organism. PET provides analysis of the metabolism. PET may be used to find tumors and metastases and to assess perfusion of the heart muscle. PET has a local resolution (approximately 5 mm), which generally cannot be increased without additional radiation exposure. PET does not provide good anatomical images, and thus the spatial localization and association of the loci of disease found presents difficulties.

The combination of PET and CT scanners is becoming increasingly popular, especially in radiation therapy. The tracers injected in a PET examination accumulate in tumors and metastases, for example, and thus make the tumors and metastases easier to locate. A CT scanner provides anatomical information, and the PET unit provides functional information, for example, about cellular activities and metabolic processes in a target volume. In combination, both geometric and functional information about the turner or metastates may be used for determining the target region, when planning for radiation therapy.

DE 10 2005 048 853 discloses a combination of a PET unit with a 3D X-ray system, such as a cone beam CT scanner. The PET unit and the 3D X-ray system are, for example, located side by side, so that a patient lying on a patient examination or treatment table may be moved in succession to the two imaging units.

For radiation therapy, the same patient mount may be used both in radiation planning and for the radiation; for example, structurally identical patient mounts are used. Using the same patient mount increases the precision in radiation therapy, since mechanical imprecision's are the same in both cases.

In PET-CT combination units in the prior art, in particular robotic patient positioning units, which have an engagement point of the support arm below the stretcher, for instance, cannot use the same patient mount. The support arm would collide with the "front" imaging units when the patient is moved into the "rear" imaging unit. Thus, there is a need for a combination unit with stretchers and patient positioning units that may be used for radiation planning and for the radiation itself.

SUMMARY

The present embodiments may obviate one or more of the drawbacks or limitations of the related art. For example, in one embodiment a combination PET and tomography device includes a robotic patient positioning device that may be used for radiation planning and for radiation treatment.

In one embodiment, a detector ring system of a PET system has an angular region without detector elements. The PET system has an open, not closed, detector ring. A patient mounting element, such as a robot arm engaging a patient examination or treatment table may be introduced into the opening of the detector ring system. The ring may be a split ring, or it may have a recess with a supporting connection provided at a sufficient distance.

The patient mounting element, such as a stretcher (support) or patient examination or treatment table, may be positioned in the PET system or in the tomography device for the 3D imaging. A patient mounting device may include the patient mounting element and the stretcher. A patient may lie on the stretcher. When the patient is positioned in the medical imaging unit, for example, in the tomography device for 3D imaging and/or in the PET system, the patient mounting element, in the positioning of the patient, is moved at least partway into the recess of the non-closed detector ring system.

A support, for example, with a robotic patient mounting system, may be moved to inside the tomography device through the open angular region. The PET system may be located in front of the tomography device from the standpoint of the patient. With respect to the radiation therapy session, the same mechanical imprecision in positioning the patient exists both in the imaging and in the radiation treatment, so that systematic errors may be reduced. Systematic errors cause a deviation from the planned dosage application.

In one embodiment, the medical imaging unit includes a patient mounting device for introducing a patient both into the PET unit and into the tomography device. This patient mounting device includes the patient mounting element. The recess in the detector ring is adapted to the size of the patient mounting element. The patient mounting element may be moved into the recess in the non-closed detector ring system when positioning the patient. The patient mounting device may include a stretcher or support, which is suitable for use in a radiation therapy system, such as a particle therapy system.

The opening of the PET system may be under, laterally under, or laterally next to the patient examination or treatment table. The location of the opening of the PET system depends on the engagement point on the stretcher.

In one embodiment, the medical imaging unit has a PET system with at least one foldable detector segment. In a PET examination, the at least one foldable detector segment covers the open angular region and folds to the side for an X-ray examination. Instead of being foldable, such a detector element may also be slidable, or it may be insertable into the open angular region and removable from it again in some other way.

The tomography device may be, for example, a CT scanner, cone beam CT scanner, or magnetic resonance tomography device.

A medical imaging unit may be used to obtain image data sets for radiation therapy planning and/or for position verification in a radiation therapy system. The medical imaging unit may use the above-described embodiments, principles, or description to obtain the image data sets.

BRIEF DESCRIPTION OF THE DRAWINGS

FIG. 1 illustrates one embodiment of a medical imaging unit with a PET system and a tomography device;

FIG. 2 illustrates one embodiment of a medical imaging unit with a PET system and a C-arm X-ray system;

FIGS. 3 and 4 illustrate a PET system with foldable detector elements in the folded-up and unfolded state; and FIG. 5 illustrates a PET system with a laterally disposed opening.

DETAILED DESCRIPTION

In one embodiment, as shown in FIG. 1, a medical imaging unit 1 may include a PET system 3 and a tomography device 5, such as an X-ray or magnetic resonance computed tomography device. The PET system 3 has a detector ring, which is not completely closed. The detector ring includes a ring opening. The ring opening is a free angular region that may be oriented downward. The PET system may also include a central opening. The central opening is generally surrounded by the detector ring. The ring opening is a passage from outside the detector ring to the central opening. For example, as illustrated in FIG. 5, a stretcher 9 may pass from outside of the detector ring to the central opening with a portion of a support of the stretcher 9 passing through the ring opening.

A patient 7, lying on a stretcher 9, may be examined with the tomography device 5 using the ring opening of the PET unit 3. A support arm (e.g., robot arm) of a patient mount 11 engages an engagement point 14 via a connecting element 13 below the stretcher 9 (e.g., patient support). When the patient 7 is moved into the medical imaging unit 1, the connecting element 13 and the support arm may be moved into the medical imaging unit 1 far enough that the support arm is located in the ring opening, and/or may be moved through the ring opening. Support systems (e.g., robots) used in radiation therapy may be used for patient positioning in examination using the medical imaging unit 1. The ring opening in the PET unit 3 is at least wide enough (for example, approximately 10 to 20 cm) that the support arm fits through it, and/or wide enough (for example, approximately 40 to 60 cm) that the stretcher 9 fits through it to its full width. For stabilizing the detector ring, a connection may be provided in the ring opening region. The connection may be located on the side toward the tomography device. The connection may be embodied such that it leaves enough space available, for example, for the support arm, as a connecting element, to be introduced.

In one embodiment, as shown in FIG. 2, a cone beam CT scanner 15 (e.g., a C-arm X-ray system) may be used with the PET system. A cone beam CT scanner has great flexibility. The flexibility of the cone beam CT scanner may be used in combination with a PET unit 30 and a robot patient mount 11' with a stretcher 9'.

In one embodiment, as shown in FIG. 3, a PET system 33 may include two foldable detector segments 17, which may be introduced as needed into the ring opening in the PET system 33, for example, below the stretcher 9". Alternatively, one foldable detector segment may be used, for example, via a displacement mechanism. Given suitably small-sized engagement points of a robot arm, a single, for example, foldable, detector segment may bridge the ring opening in the detector ring. The detector area that is normally lacking because of the ring opening may be supplemented as needed. FIG. 3 shows the closed situation. FIG. 4 shows the operating state with detector elements folded to the side.

In one embodiment, as shown in FIG. 5, a PET system 35 includes an open angular region located laterally.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A medical imaging unit comprising:
a tomography device for 3D imaging; and
a positron emission tomography (PET) system,
wherein the PET system includes a non-closed detector ring system, which has a ring opening in an angular region, the ring opening being operable to receive a patient mounting element, and
wherein the patient mounting element comprises a support arm being operable to pass into the ring opening.

2. The medical imaging unit as defined by claim 1, wherein the angular region is located in the lower region of the detector ring system, and a patient support is retained on its underside by the patient mounting element.

3. The medical imaging unit as defined by claim 2, wherein the patient support is operable to move into a central opening of the PET system.

4. The medical imaging unit as defined by claim 1, wherein the angular region is located in the laterally lower region of the detector ring system, and a patient support is retained by the patient mounting element laterally next to or laterally below the angular region.

5. The medical imaging unit as defined by claim 4, wherein the patient support is operable to move into a central opening of the PET system.

6. The medical imaging unit as defined by claim 1, comprising:
a patient mounting device that is operable to move a patient, the patient mounting device including the patient mounting element;
wherein the patient mounting device is operable to move the patient into the PET system and into the tomography device, which is located on a first side of the PET system.

7. The medical imaging unit as defined by claim 6, wherein the patient mounting element includes a patient support, which is operable to be used in a radiation therapy system.

8. The medical imaging unit as defined by claim 7, wherein the patient support is operable to be used in a particle therapy system.

9. The medical imaging unit as defined by claim 6, wherein the patient mounting device is a robotic patient positioning unit that includes a patient support, the support arm engages the patient support at an engagement point, which is located under, laterally under, or laterally beside the patient support.

10. The medical imaging unit as defined by claim 9, wherein the robotic patient positioning unit includes a connector, which engages an engagement point on the patient support.

11. The medical imaging unit as defined by claim 10, wherein a size and a shape of the ring opening is defined by the connector.

12. The medical imaging unit as defined by claim 6, wherein the patient mounting device is located on a side of the PET system that is opposite to the side the tomography device is located.

13. The medical imaging unit as defined by claim 1, comprising:
   a detector segment that is operable to cover at least a portion of the ring opening and be moved to open the ring opening.

14. The medical imaging unit as defined by claim 13, wherein the detector segment is operable to be folded into and out of the ring opening.

15. The medical imaging unit as defined by claim 1, wherein the tomography device includes an X-ray system, cone beam, or magnetic resonance computed tomography device.

16. The medical imaging unit as defined by claim 1, wherein the ring opening is sized and shaped to receive the patient mounting element.

17. A method for obtaining sets of image data for radiation therapy planning and/or for position verification in a radiation therapy session, the method comprising:
   moving a support arm, which connects to a patient support, through a ring opening of a detector ring of a PET system; and
   positioning the patient support in a tomography device.

* * * * *